US006737414B2

(12) United States Patent
Saniez

(10) Patent No.: US 6,737,414 B2
(45) Date of Patent: *May 18, 2004

(54) COMPOSITION FOR ENTERAL NUTRITION COMPRISING FIBRES

(75) Inventor: Marie-Hélène Saniez, Saint Andre (FR)

(73) Assignee: Roquette Freres, Lestrem (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/113,470

(22) Filed: Mar. 29, 2002

(65) Prior Publication Data

US 2003/0039740 A1 Feb. 27, 2003

(30) Foreign Application Priority Data

Mar. 30, 2001 (FR) .............................. 01 04413

(51) Int. Cl.$^7$ ..................... A61K 31/715; C08B 37/16
(52) U.S. Cl. ..................... 514/58; 514/738; 536/103; 536/124
(58) Field of Search .................. 514/58, 738; 536/103, 536/124

(56) References Cited

U.S. PATENT DOCUMENTS 5,837,060 A * 11/1998 Fouache nee Ducroquet et al. .......................... 127/36
5,952,314 A 9/1999 DeMichele et al. ........... 514/54

FOREIGN PATENT DOCUMENTS

| EP | 0 756 828 | 11/1998 |
| EP | 1 010 374 | 6/2000 |
| WO | WO 95/02969 | 2/1995 |

OTHER PUBLICATIONS

Internet site of Matsutani Chemical Industry Co., Ltd., abstract N° XP002185032, no date listed.

* cited by examiner

Primary Examiner—Dwayne C. Jones
(74) Attorney, Agent, or Firm—Sturm & Fix LLP

(57) ABSTRACT

The subject of the invention is a fiber-enriched composition for enteral nutrition, characterized in that it comprises 0.5 to 20%, preferably 1 to 10%, and still more preferably 1 to 5% by dry weight of branched maltodextrins having between 15 and 35% of 1→6 glucoside linkages, a reducing sugar content of less than 20%, a polymolecularity index of less than 5 and a number-average molecular mass Mn at most equal to 4500 g/mol.

11 Claims, 1 Drawing Sheet

Figure 1:
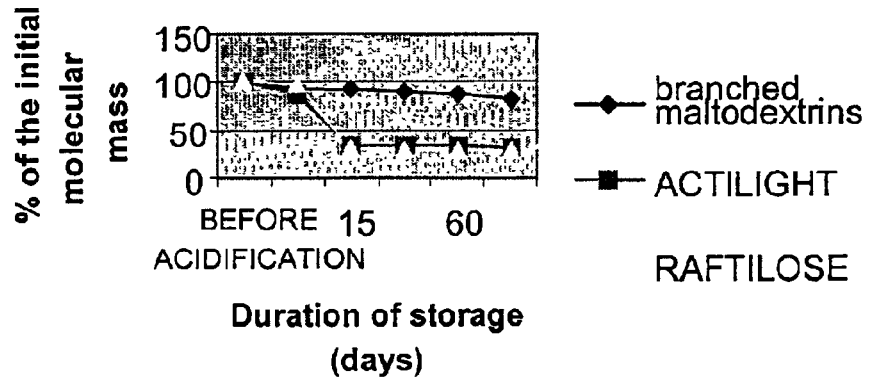
Figure 1:
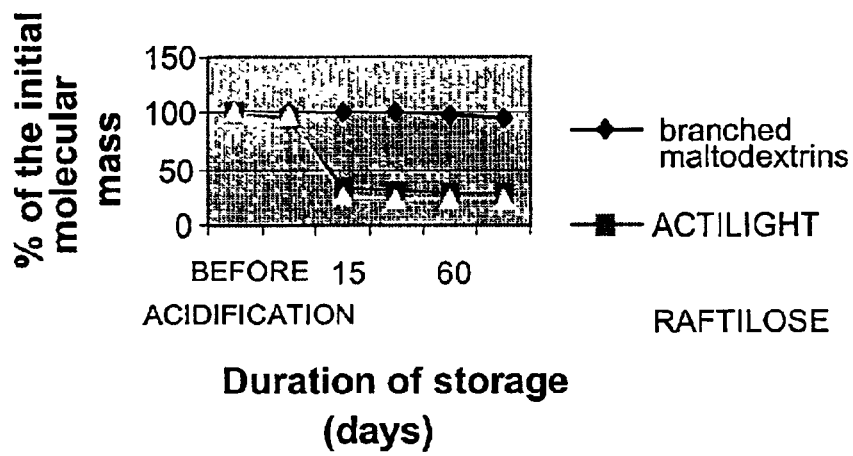

Variation of the number-average molecular mass, in solution at 10% pH 2.7.

Variation of the weight-average molecular mass, in solution at 10%, pH 2.7.

COMPOSITION FOR ENTERAL NUTRITION COMPRISING FIBRES

FIELD OF THE INVENTION

The invention relates to a composition for enteral nutrition comprising fibres.

BACKGROUND OF THE INVENTION

More precisely, the object of the invention is a composition for enteral nutrition comprising branched maltodextrins.

Artificial nutrition makes it possible, in adults as in children, to compensate for a defective intestine, to put an inflammatory intestine to rest, to correct severe undernourishment in a patient unable or unwilling to eat, either because of a serious condition, or because of a cumbersome treatment. Its duration can extend from a few days to four weeks to several months or years. Depending on the cases, the artificial nutrition will be performed by the digestive route (enteral nutrition) or by the venous route (parenteral nutrition). Always introduced in a hospital setting, in medicine, surgery and intensive care, artificial nutrition can now be continued at home in cases requiring a very prolonged treatment. The basic principle of enteral or parenteral artificial nutrition is the supply of all the nutrients necessary for life: sugars, fats, proteins, minerals, trace elements, vitamins, which the subject can no longer take in by the usual oral route.

Enteral nutrition is the most simple and the most physiological route for nutritive assistance. The site of delivery is in general intragastric, with the aid of a tube introduced by the nasal route. An effective and well-tolerated enteral nutrition involves two basic technical principles: the slowness (1 to 3 ml/min) and the continuous nature (from 12 h to 24 h per day) of the food instillation.

In the case of extensive intestinal lesions compromising the functions of absorption, the foods used are predigested (amino acids, monosaccharides).

When the small intestine is still functional, a semi-basic diet composed of less degraded, or even nondegraded, nutrients is used. Minerals, trace elements and vitamins, are added systematically and daily. The nutrients are prepared, mixed and stored under conditions of strict cleanliness, or even asepsis in case of industrial preparation.

Hospitalized patients and in particular patients on antibiotics or suffering from intestinal disorders, resulting either in constipation, or in diarrhoeas and receiving nutritional assistance by the enteral route need a supply of appropriate fibre.

The fibres are recognized for their beneficial effects on human health and should form an integral part of the daily food supplies. Fibres are generally classified into two categories: soluble fibres and insoluble fibres. Soluble fibres, such as pectin, inulin, resistant starches are fermented by the intestinal bacterial flora. This fermentation releases short-chain fatty acids in the colon, which have the effect of reducing the pH thereof and consequently of limiting the development of pathogenic bacteria.

Insoluble fibres, such as cellulose, maize or soya bean fibres have an essentially mechanical role in the gastrointestinal tract. They are only very slightly fermented by the intestinal flora and contribute to reducing the duration of the intestinal transit.

A fibre-enriched composition for enteral nutrition should ideally:

be similar to the fibres conventionally consumed;

generate a production of beneficial volatile fatty acids;

not cause flatulence in the patient;

improve intestinal motility;

not have residues;

be soluble;

have adequate viscosity so as to facilitate its instillation;

be stable during storage and during sterilization;

be gradually assimilated;

promote mineral absorption.

Several compositions for enteral nutrition containing fibres have been proposed. Pectin fibres have been proposed, but have disadvantages such as an excessively high viscosity, and a lack of improvement in mineral absorption.

Patent EP-B1 0,756,828 describes fibre-enriched compositions, containing a mixture of soluble fibres, insoluble fibres and resistant starch. These compositions contain a high proportion of soluble fibres and have a high viscosity which is not suited to instillation by a tube. These compositions also have problems of stability.

The document EP-A1 1,010,374 describes a mixture of fibres for enteral nutrition comprising soluble and insoluble pea fibres, inulin and fructooligosaccharides. These compositions are also too viscous especially because of the presence of pea fibres and inulin which are scarcely soluble; the fructooligosaccharides are not stable during sterilization. This instability results in gradual hydrolysis, which generates a release of glucose and fructose and a colour which are undesirable. These mixtures of fibres only partially promote mineral absorption, and are not gradually assimilated. Moreover, the pea fibres and inulin generate problems of flatulence in the patient. As for the fructooligosaccharides, these molecules remain poorly tolerated by the body, which is expressed by the onset of diarrhoea.

SUMMARY OF THE INVENTION

The aim of the present invention is therefore to remedy the disadvantages of the prior art. The applicant has indeed found that the incorporation of the said branched maltodextrins into a composition for enteral nutrition advantageously makes it possible to reconcile all these objectives which have up until now been reputed irreconcilable by devising and producing, at a cost of numerous research studies, a novel fibre-enriched composition for enteral nutrition which meets all the abovementioned criteria, namely the viscosity, the solubility, a satisfactory stability during storage and during sterilization manifested by the absence of retrogradation, a gradual assimilation, an absence of generation of flatulence, and a considerable improvement in mineral, and in particular calcium and magnesium, absorption.

DETAILED DESCRIPTION OF THE INVENTION

The subject of the invention is therefore a fibre-enriched composition for enteral nutrition, characterized in that it comprises branched malto-dextrins having between 15 and 35% of 1→6 glucoside linkages, a reducing sugar content of less than 20%, a polymolecularity index (ratio of weight-average molecular mass over number-average molecular mass) of less than 5, and a number-average molecular mass Mn at most equal to 4500 g/mol.

The expression branched maltodextrins is understood to mean, for the purposes of the present invention, the maltodextrins described in patent application EP 1,006,128 of which the assignee is proprietor. These branched maltodextrins have an indigestibility character which has the consequence of reducing their calorific value, by preventing their assimilation in the small intestine. They therefore represent a source of indigestible fibres beneficial to the metabolism and the intestinal balance. As a guide, their insoluble fibre level is generally greater than 506 on a dry matter basis. Their high content of 1→6 glucoside linkages confers quite particular prebiotic properties on them: it has indeed appeared that the bacteria of the cæcum and of the colon of humans and of animals, such as butyrogenic, lactic or propionic bacteria, metabolize highly branched compounds. Moreover, these branched maltodextrins promote the development of the bifidogenic bacteria to the detriment of the undesirable bacteria. This results in properties which are quite beneficial to the health of the consumer. Finally, the branched character of the said maltodextrins considerably and advantageously reduces their tendency to undergo retrogradation, which makes it possible to envisage their use in applications where the absence of retrogradation is necessary, in particular during prolonged storage in aqueous solution.

All the branched maltodextrin compositions described in patent application EP 1,006,128 and its US counterpart (U.S. Pat. No. 09/455,009; Assignee Roquette Frères) are appropriate for the preparation of compositions for enteral nutrition according to the invention. The entire content of U.S. Ser. No. 09/455,009 is herein incorporated by reference.

According to a preferred variant, they have a reducing sugar content of between 2 and 5% and a number-average molecular mass of between 2000 and 3000 g/mol.

According to another advantageous variant, all or some of these branched maltodextrins are hydrogenated, they are thus advantageously even more stable during sterilization.

A fibre-enriched composition for enteral nutrition in accordance with the invention comprises 0.5 to 20%, preferably 1 to 10%, and still more preferably 1 to 5% by dry weight of branched maltodextrins so as to constitute a fibre supply and a sufficient energy supply. The branched maltodextrins have an insoluble fibre level greater than 50% on a dry basis, determined according to the AOAC No. 985-29 method (1986). Below 0.5% by weight of maltodextrins in the composition for enteral nutrition in accordance with the invention, the fibre supply is insufficient to have a detectable effect.

The apparent improvement in the absorption of calcium and magnesium is shown in particular in animals and leads to remarkable results as will be otherwise exemplified, making it possible to envisage the preparation of compositions for enteral nutrition which improve the calcium and magnesium status of the patient. This is surprising and unexpected for fibre-rich compounds whose negative influence on the absorption of mineral elements is known.

It was moreover found that the branched maltodextrins according to the invention did not generate osmotic diarrhoeas, even at high doses. The phenomenon of osmotic diarrhoea is observed during absorption of low-molecular weight fermentable carbohydrates, such as for example lactulose or fructooligosaccharides. This phenomenon results in an increase in the water content of stools in reaction to an increase in the osmolarity of the faecal content, it being possible for this increase in water content to extend as far as the appearance of diarrhoeas. Surprisingly, and unexpectedly, the branched maltodextrins in accordance with the invention do not generate this phenomenon although they are fermentable.

The composition for enteral nutrition in accordance with the invention also comprises a source of proteins, lipids and carbohydrates. Preferably, the proteins represent about 10 to 20% of the energy supply of the composition. They are, for example, supplied by animal proteins such as milk proteins, or soya bean proteins or alternatively proteins of cereal origin. They may be provided in native or hydrolysed form so as to provide a source of free amino acids.

The lipids preferably constitute 30 to 50% of the energy supply of the composition, in the form of monounsaturated, polyunsaturated and saturated fatty acids. Any oil is indeed suitable, such as for example olive, maize, sunflower, wheat and oils.

The carbohydrates, other than the said branched maltodextrins, preferably represent 35 to 55% of the energy supply. They may be provided by standard or modified starches, high amylose starches, modified or otherwise, standard maltodextrins, simple sugars. The branched maltodextrins according to the invention may of course constitute both an energy supply and a fibre supply.

The composition for enteral nutrition according to the invention may also be supplemented with a complete vitamin and mineral supply. Flavourings, sweeteners and other additives may also be added.

Although not a preferred variant of the invention, the said branched maltodextrins may be completely or partially replaced with indigestible dextrins such as in particular FIBERSOL® marketed by the company MATSUTANI. However, as the latter are low in insoluble fibres, they are advantageously mixed with the said branched maltodextrins.

Accordingly, the composition for enteral nutrition in accordance with the invention may comprise branched maltodextrins mixed with indigestible dextrins.

The said composition may be provided in a ready-to-use form, that is to say in a form which can be instilled by means of a gastric tube, or alternatively in the form of a drink such as a fruit juice, a soup or a milk shake, or alternatively in the form of dessert creams or yoghurts directly consumed by the patient or which can be administered by a tube.

The said composition may also be provided in the form of a powder to be reconstituted in a liquid.

The branched maltodextrins according to the invention exhibit a stability in acidic medium and a stability to heat treatments which are quite advantageous when it is desired to prepare compositions for enteral nutrition at slightly acidic to acidic pH, such as, for example drinks, soups or fruit juices. This stability has not been observed for fructooligosaccharides. Furthermore, when compositions are prepared which are intended to be sterilized, it is often preferred that these compositions are slightly acidic so as to avoid the caramelization of the sugars during the heat treatment. The stability of the branched maltodextrins in acidic medium and/or to heat is therefore quite advantageous and appropriate.

The composition for enteral nutrition, whether it is solid or liquid, will be preferably sterilized by any technique known to persons skilled in the art and packaged, if necessary, in boxes, pouches or sterile bottles.

The preparation per se of the liquid or solid composition for enteral nutrition may be carried out by any conventional technique, consisting, for example, in simply mixing the various powdered ingredients, or in spray-drying a solution comprising all the said ingredients. When a liquid form is involved, the said composition should be easily administerable by means of a tube, or by mere gravity, or by pumping. It should then have a reduced viscosity, for example of less than 40 mPa.s at room temperature.

The said composition for enteral nutrition may be used in animals.

The invention will be understood more clearly on reading the examples which follow and the FIGURE relating thereto and which are intended to be illustrative and nonlimiting.

EXAMPLE 1

Demonstration of Mineral Absorption

A group of rats is fed with mixtures of standard food containing 5 to 10% by dry weight of branched maltodextrins in accordance with the invention. A control group receives the standard food.

Group 1 receives standard food. Group 2 receives food mixed with 5% of branched maltodextrins, and group 3 receives food mixed with 10% of branched maltodextrins. The trial is carried out for 14 days, at the end of which an evaluation of calcium and magnesium is carried out by analysing the calcium and magnesium in the stools, in the food and in the drinking water distributed to the animals.

The following results are obtained:

|  | CALCIUM | | MAGNESIUM | |
| --- | --- | --- | --- | --- |
|  | INTESTINAL ABSORPTION* (%) | VARIATION RELATIVE TO GROUP 1 (%) | INTESTINAL ABSORPTION | VARIATION RELATIVE TO GROUP 1 (%) |
| GROUP 1 | 21.52 | — | 32.74 | — |
| GROUP 2 | 29.62 | +37.6 | 39.34 | +20.2 |
| GROUP 3 | 38.49 | +78.9 | 47.8 | +46.0 |

*the intestinal absorption is calculated by subtracting the level of the mineral considered in the stools from the level of the same mineral in the food and in the drink, expressed as a percentage.

These results clearly demonstrate the completely positive influence of a supply of branched maltodextrins in the diet of the rats on the absorption of the minerals in the digestive tract, which is quite surprising for high-fibre compounds whose unfavourable effects on the absorption of mineral elements are known.

EXAMPLE 2

Preparation of the Composition for Enteral Nutrition according to the Invention A composition for enteral nutrition is prepared by mixing, in distilled water, branched maltodextrins of the following composition:

| Reducing sugars | 2.3 |
| --- | --- |
| Mn (g/mol) | 2480 |
| Mw (g/mol) | 5160 |
| 1,2 linkage (%) | 10 |
| 1,3 linkage (%) | 12 |
| 1,4 linkage (%) | 49 |
| 1,6 linkage (%) | 29 |

To this solution are added a mixture of maize, rapeseed and soya bean oils, a mixture of milk proteins and soya bean proteins, a standard maltodextrin, as well as vitamins and minerals.

The composition obtained is described below (% by weight):

proteins: 4% carbohydrates: 11 lipids: 4% branched maltodextrins: 3% insoluble fibres: 1.5%

The composition obtained is stored for six months, after which the stability during storage is evaluated: the composition is homogeneous and has no crystals or sediments, indicating an absence of retrogradation and therefore a good stability during storage, and making it possible to envisage, for the compositions in accordance with the invention, an expiry date above six months.

EXAMPLE 3

Study of Stability in Solution

In order to assess the stability of the branched maltodextrins in drinks, solutions are prepared at different pH values, containing either fructo-oligosaccharides (ACTILIGHT 950P marketed by BEGHIN-SAY or RAFTILOSE P35 marketed by ORAFTI), or branched maltodextrins in accordance with the invention.

The variation of the molecular masses of these oligosaccharides in solution is measured during storage by steric exclusion followed by differential refractometric detection.

The results are illustrated in FIG. 1.

In the case of the branched maltodextrins, a very slight effect of the acidification of the solutions is observed. There is therefore a slight hydrolysis at the very acidic pH values (less than 3) which results in a variation of the molecular weight towards lower values. After two weeks of storage, the differences are not greater than those observed immediately after acidification. After 1 month of storage, only the values obtained for the very low pH values (less than 2.7) decreased relative to two weeks ageing. The number-average molecular weight passes from 2800 daltons to 2400 daltons for solutions at pH 2.

In the case of the fructooligosaccharides, after two weeks of storage at pH 2, the molecular weight is reduced to 30% of its initial value. After 1 month, the solutions at pH 2 and 2.7 contain very highly degraded fructooligosaccharides.

Conclusion: the branched maltodextrins are well suited to the preparation of drinks, of fruit or vegetable juices, having a pH generally less than 3.

EXAMPLE 4

Stability to Heat Treatment

Fruit juices comprising branched maltodextrins according to the invention are prepared which are subjected to a pasteurization treatment for 17 minutes at 74° C. A control without branched maltodextrins and a control comprising fructooligosaccharides are also prepared. The contents are compared before and after treatment, as well as after storage. All the fruit juices have a pH of 3.8.

The results are given by the following table:

|  | CONTROL | 7% branched maltodextrins | | 7% hydrogenated branched maltodextrins | | 7% fructooligo-saccharides (ACTILIGHT ®) | |
|---|---|---|---|---|---|---|---|
|  | Sucrose | Sucrose | Branch. malt. | Sucrose | Hydrogenated branch. malt. | Sucrose | FOS |
| Before pasteurization | 2.5 | 2.4 | 7.0 | 2.1 | 6.8 | 2.3 | 6.7 |
| After pasteurization | 1.4 | 1.6 | 7.0 | 1.6 | 6.8 | 2.4 | 4.5 |
| After pasteurization + 1.5 months | nd | nd | 6.9 | nd | 6.9 | 3.8 | 2.4 |
| After pasteurization + 3 months | 1.5 | 1.5 | 7.1 | 1.2 | 7.1 | 3.4 | 1.7 |

These results demonstrate the absence of degradation of the branched maltodextrins according to the invention, hydrogenated or otherwise, because they are neither hydrolysed during the heat treatment, nor during storage for three months. The fructooligosaccharides become highly degraded with pasteurization (−30%) and with storage (−60% after three months compared with the value after pasteurization). This is observed both through the reduction in the FOS level and through the increase in the content of sucrose (product of hydrolysis). This confirms the most particular advantage of the maltodextrins according to the invention in compositions for enteral nutrition intended in particular to be sterilized or pasteurized.

What is claimed is:

1. A fibre-enriched composition for enteral nutrition, comprising 0.5 to 20% by dry weight of branched maltodextrins having between 15 and 35% of 1→6 glucoside linkages, a reducing sugar content of less than 20%, a polymolecularity index of less than 5 and a number-average molecular mass Mn at most equal to 4500 g/mol.

2. The fibre-enriched composition for enteral nutrition according to claim 1 comprising 1 to 10% by dry weight of branched maltodextrins having between 15 and 35% of 1→6 glucoside linkages.

3. The fibre-enriched composition for enteral nutrition according to claim 2 comprising 1 to 5% by dry weight of branched maltodextrins having between 15 and 35% of 1→6 glucoside linkages.

4. The fibre-enriched composition for enteral nutrition of claim 1, wherein said branched maltodextrins have a reducing sugar content of between 2 and 5% and a number-average molecular mass Mn of between 2000 and 3000 g/mol.

5. The fibre-enriched composition for enteral nutrition of claim 1, wherein all or some of the said branched maltodextrins are hydrogenated.

6. The fibre-enriched composition for enteral nutrition of claim 1, which further comprises proteins, and/or lipids, and/or carbohydrates, vitamins and minerals.

7. The fibre-enriched composition for enteral nutrition of claim 1, which as a powder to be reconstituted.

8. The fibre-enriched composition for enteral nutrition of claim 1, which is a ready-to-use composition.

9. The fibre-enriched composition for enteral nutrition of claim 1, wherein said branched maltodextrins have an insoluble fibre level greater than 50% on a dry matter basis.

10. The fibre-enriched composition for enteral nutrition of claim 1, wherein said branched maltodextrins are mixed with indigestible dextrins.

11. The fibre-enriched composition for enteral nutrition of claim 1, wherein said branched maltodextrins are stable under acidic conditions and/or to heat.

* * * * *